(12) United States Patent
Zauner

(10) Patent No.: US 7,776,003 B2
(45) Date of Patent: Aug. 17, 2010

(54) MULTIMODAL CATHETER FOR FOCAL BRAIN MONITORING AND VENTRICULOSTOMY

(76) Inventor: Alois Zauner, 324 E. Rivo Alto Dr., Miami Beach, FL (US) 33139

( * ) Notice: Subject to any disclaimer, the term of this patent is extended or adjusted under 35 U.S.C. 154(b) by 653 days.

(21) Appl. No.: 11/554,008

(22) Filed: Oct. 28, 2006

(65) Prior Publication Data

US 2008/0171990 A1    Jul. 17, 2008

(51) Int. Cl.
*A61M 5/00* (2006.01)
*A61M 5/32* (2006.01)

(52) U.S. Cl. .................. 604/9; 604/174; 604/175

(58) Field of Classification Search ......... 604/523–532, 604/95.01–95.05, 9, 174, 175
See application file for complete search history.

(56) References Cited

U.S. PATENT DOCUMENTS

| | | | |
|---|---|---|---|
| 3,949,757 A | 4/1976 | Sabel | |
| 4,217,910 A | 8/1980 | Khalil | |
| 4,292,976 A | 10/1981 | Banka | |
| 4,377,169 A | 3/1983 | Banks | |
| 4,432,853 A | 2/1984 | Banks | |
| 4,602,645 A | 7/1986 | Barrington et al. | |
| 4,613,324 A | 9/1986 | Ghadjar | |
| 4,624,265 A | 11/1986 | Grassi | |
| 4,632,668 A | 12/1986 | Wilson, Jr. et al. | |
| 4,655,745 A | 4/1987 | Corbett | |
| 4,723,556 A | 2/1988 | Sussman | |
| 4,767,400 A | 8/1988 | Miller et al. | |
| 4,784,638 A | 11/1988 | Ghajar et al. | |
| 4,903,707 A | 2/1990 | Knute et al. | |
| 4,911,174 A | 3/1990 | Pederson et al. | |
| 4,931,039 A | 6/1990 | Coe et al. | |
| 4,953,559 A | 9/1990 | Salerno | |
| 4,970,926 A | 11/1990 | Ghajar et al. | |
| 5,172,699 A | 12/1992 | Svenson et al. | |
| 5,180,387 A | 1/1993 | Ghajar et al. | |
| 5,352,207 A | 10/1994 | Nussbaum | |
| 5,531,673 A | 7/1996 | Helenowski | |
| 5,690,117 A | 11/1997 | Gilbert | |
| 5,738,666 A | 4/1998 | Watson et al. | |
| 6,453,185 B1 | 9/2002 | O'Keefe | |
| 6,626,902 B1 * | 9/2003 | Kucharczyk et al. | 606/41 |
| 6,749,574 B2 | 6/2004 | O'Keefe | |

(Continued)

OTHER PUBLICATIONS

Zauner et al., "Continuous Monitoring of Cerebral Substrate Delivery and Clearance: Initial Experience in 24 Patients with Severe Acute Brain Injuries," Neurosurgery, Nov. 1997, pp. 1082-1093, vol. 41, No. 5.

*Primary Examiner*—Kevin C Sirmons
*Assistant Examiner*—Imani Hayman
(74) *Attorney, Agent, or Firm*—Loren Donald Pearson; Assouline & Berlowe

(57) ABSTRACT

A ventricular catheter includes an external ventricular drainage (EVD) catheter and has at least one conduit formed in the wall of the EVD catheter. The conduit opens at a side port of the wall at an angle to the EVD catheter. The side port is formed in the wall to allow a probe to be extended from the conduit at the angle into brain tissue that is not altered by the insertion of the EVD catheter. The ventricular catheter has an oval shape to minimize the total cross-sectional area while still allowing the necessary number of conduits.

33 Claims, 3 Drawing Sheets

U.S. PATENT DOCUMENTS

| | | |
|---|---|---|
| 6,761,718 B2 | 7/2004 | Madsen |
| 6,847,839 B2 | 1/2005 | Ciaccio et al. |
| 6,871,740 B1 | 3/2005 | Cao |
| 6,955,657 B1 | 10/2005 | Webler |
| 7,070,579 B1 | 7/2006 | Harper |
| 7,160,296 B2 * | 1/2007 | Pearson et al. ............... 606/42 |

* cited by examiner

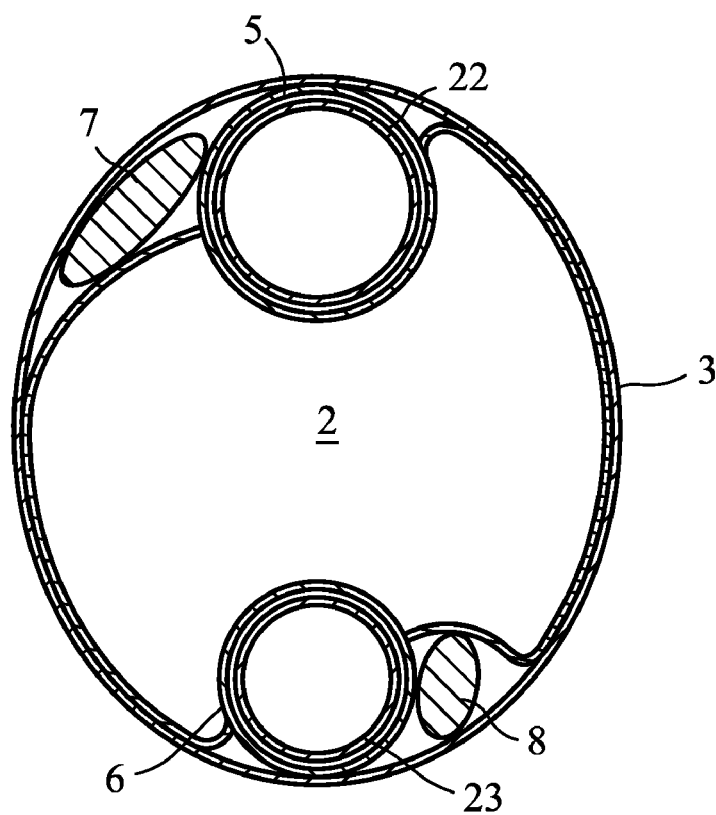
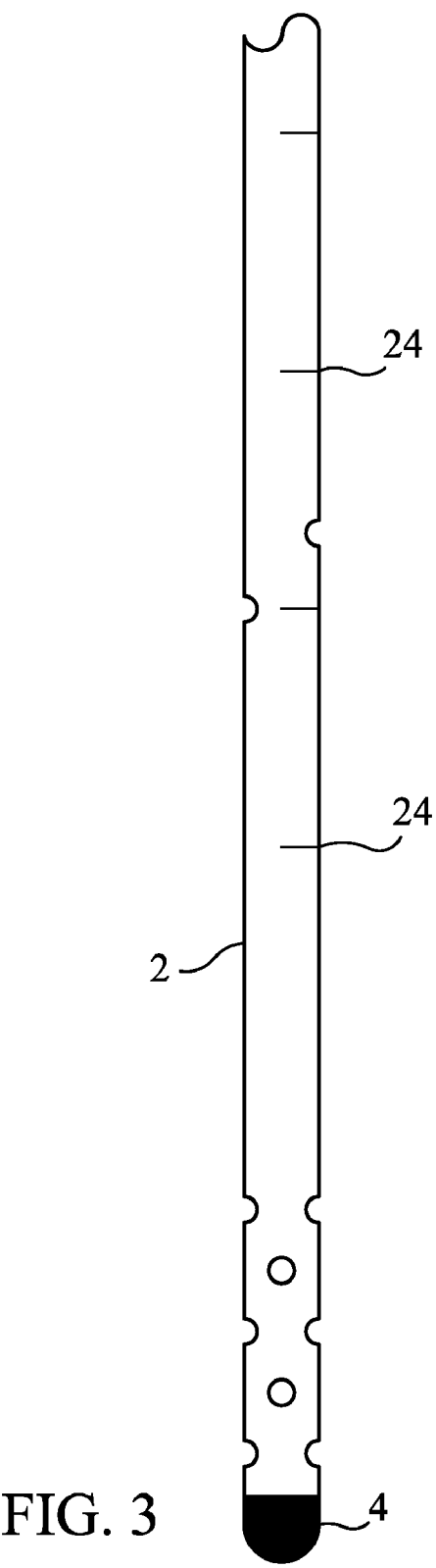
FIG. 2
FIG. 3

MULTIMODAL CATHETER FOR FOCAL BRAIN MONITORING AND VENTRICULOSTOMY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The invention relates to ventricular catheters and more particular to multimodal catheters for focal brain monitoring and ventriculostomies.

2. Description of the Related Art

External ventricular drainage catheters are known in the art. External Ventricular Drainage (EVD) catheters are indicated for drainage of cerebrospinal fluid (CSF) from the lateral ventricles of the brain and for relieving intracranial pressure. A typical EVD catheter has a length of fifteen to thirty-five centimeters (15-35 cm) with an outer diameter between two and one half and three and three tenths millimeter (2.5-3.3 mm) and an inner diameter between one and three tenths and one and nine tenths millimeter (1.3-1.9 mm). A stylet is typically used for inserting the distal end of the EVD catheter into the brain tissue and a trocar is used for the proximal subcutaneous insertion. A Luer connector can be added at the proximal end of the EVD catheter. Easy to see length depth markers have been taught for aiding in quick insertion. EVD catheters exist that are translucent with a barium impregnated stripe allowing for both immediate visualization of CSF and radio-opacity. A number of lateral holes are included to allow the CSF to enter the EVD catheter.

Prior-art EVD catheters are typically inserted according to the following procedure. The patient is given a local aesthetic at the location of insertion. A first incision is made in the skin on the head at the location of insertion. The skull is drilled. The catheter is then inserted to a depth of five and five tenths to six centimeters (5.5-6.0 cm) to reach the lateral ventricle. CSF under pressure from cranial injury, inflammation, hemorrhage, or the like can be vented externally by the EVD catheter. To prevent infection, a second incision is made in the skin, the EVD catheter is tunneled to the second incision and the first incision is closed. The tunneling procedure closes a direct opening to exposed brain.

Monitoring, in particular continuous monitoring of the brain tissue surrounding an injury has been found to be an important diagnostic tool. See Zauner, Alois et al., "Instruction for Continuous Multiparameter Monitoring of Substrate Delivery and Brain Metabolism;" and Zauner, Alois, "Brain Tissue Monitoring in Critical Neurosurgical Patients: User Guide for the Neurotrend in the ICU and during Critical Cerebrovascular Surgery."

When a ventriculostomy is performed, the insertion of the EVD catheter creates microhemorrhages in the surrounding brain tissue. The microhemorrhages change some of the qualities of the brain tissue. The microhemorrhages range between two and four hundred microns (2-400 μm) deep into the tissue. Measurements made by various sensors or catheters in the tissue having microhemorrhages have been found to be inaccurate and not characterize the underlying brain tissue.

Sensors have been used with EVD catheters. These sensors are generally threaded coaxially with the EVD catheter. That is, the sensors extend alongside the EVD catheter. Therefore, the sensors are measuring the damaged tissue surrounding the EVD catheter and not undamaged neighboring brain tissue.

Placing sensors on an opposing side from an EVD catheter to avoid microhemorrhages created by EVD catheter insertion is not recommended. Insertion catheters into both hemispheres of the brain can lead to loss of speech and/or memory.

Another problem with the prior art is the connectors for the sensors. The prior art uses large plastic or metallic bolts to connect the sensors to the corresponding leads and monitors. The bolts are bulky (approximately, 5 cm by 4 cm by 1 cm) and have no means for connecting to the EVD catheter. Patients often move, brush, or even remove the bolt accidentally. In addition, the bolt's weak connection fails to prevent infection.

Another problem with the prior-art EVD systems is that the sensor cannot be added subsequent to the insertion of the EVD catheter. The sensor or sensors in prior-art systems are inserted simultaneously with the EVD catheter and alongside the EVD catheter. Therefore, once the EVD catheter is inserted, additional sensors cannot be added without removing the EVD catheter and inserting a replacement. In addition, surgeons avoid using all of the possible sensors with every EVD catheter because the sensors are often very expensive so using them without a specific reason is prohibitive. Manipulating the EVD catheter and/or sensors once they are placed requires reopening of the incision and this significantly increases the infection risk.

A related problem is that the sensors are only approved to be inserted for four to seven days. This time is frequently less than the desired insertion time for EVD catheters. Many critical patients have EVD catheters that remain inserted for more than ten days. Therefore, there is a need in the prior art to provide a means for adding sensors and catheters independently of the insertion of the EVD catheter.

An additional problem with the prior art is that the sensor is added coaxially along with the EVD catheter. As the number of sensors and catheters increases, the total cross section increases. Of course, when brain tissue is being damaged, an object is to affect as little as possible. Accordingly, an object of the invention is to provide a system that allows sensors and catheters to be included while consuming a minimal cross section.

BRIEF SUMMARY OF THE INVENTION

It is accordingly an object of the invention to provide a ventricular catheter for extended multimodality monitoring of critical neurosurgical and neurological patients after traumatic brain injury (TBI), subarachnoid hemorrhages (SAH), and stroke that overcomes the above-mentioned disadvantages of the heretofore-known devices and methods of this general type.

With the foregoing and other objects in view there is provided, in accordance with the invention, a ventricular catheter having an external ventricular drainage (EVD) catheter. An enclosed wall (i.e. closed upon itself, like a tube) forms the EVD catheter. The wall of the EVD catheter has at least one conduit formed therein. The conduit runs along the length of the EVD catheter. The conduit opens externally (i.e. toward the surround brain tissue) at a side port. The side port is formed at an angle. A probe can be deployed by inserting the probe into the conduit. For purposes of the instant application, a "probe" is meant to mean any instrument (such as a sensor or catheter) that is used to interact with and/or measure surrounding tissue. As the probe extends from the conduit at the side port, the probe extends into the surrounding brain tissue at the same angle as the side port. This allows the probe to reach beyond the brain tissue that is immediately surrounding the EVD catheter. The tip of the probe does not need to be further than one centimeter laterally from the EVD catheter. A suitable depth can be reached by extending the sensor at an angle to a length of 1.0 to 1.5 centimeters from the EVD catheter. The probe can reach brain tissue that was not damaged by the insertion of the EVD.

As discussed previously, the probe can be a sensor. The sensor is inserted into the conduit and extended from the side port into surrounding brain tissue at the angle of the side port. The sensor can measure a variety of brain parameters.

While many sensors can be fed through one of the conduits in the ventricular catheter and extended into the surrounding brain tissue, the following sensors have been found to be useful. An oxygen sensor can be used for sensing oxygen content, in particular the partial pressure of oxygen ($pO_2$), in the brain tissue neighboring the EVD catheter. A carbondioxide sensor can be used for sensing carbon dioxide content, in particular the partial pressure of carbon dioxide ($pCO_2$) in the brain tissue neighboring the EVD catheter. The sensor can be a pH sensor for measuring the pH in the brain tissue neighboring the conduit.

As discussed previously, the probe can be a catheter or more specifically a microcatheter. The microcatheter can continuously sample fluid from the surrounding brain tissue (extracellular space). In turn, the fluid can be tested. For example, the pH, glucose, pyruvate, and glutamate of the fluid being sampled can be measured.

A further (i.e. a second) conduit can be formed in the wall of the EVD catheter. Additional conduits can be formed provide that enough space is available and that the total cross-section of the ventricular catheter does not become invasive. In such a case, the wall has an additional conduit formed therein. The additional conduit opens at a respective side port of the wall. The side port is formed at an angle to project a probe at that angle into the surrounding brain tissue. Typically, the side ports are formed at the same angle but the angles are not necessarily the same.

By having a plurality of conduits surrounding the EVD catheter, a variety of sensors and probes can be inserted into the various conduits. This allows the measuring of many qualities of the brain.

A further object of the invention is to provide an EVD catheter with various conduits that has a minimal cross sectional area. When surgically inserting anything into the brain, an object is shaped to minimize the amount of brain tissue that is damaged, drilled, cut, or removed. To that end, an EVD having an oval cross section has been created. The EVD catheter that is defined by the wall has a relatively large cross section compared to the cross-sectional areas of the other conduits. The other conduits defined in the wall are relatively small. The EVD catheter has a larger diameter because the EVD catheter must have sufficient diameter to allow large amounts of spinal fluid, which can be under pressure, to be drained. The EVD catheter may have an elliptical cross section with flatter and pointier sides. The conduits are disposed along opposing sides of the EVD catheter—along the flatter sides thereof. This configuration has been found to have the least cross section while providing the necessary outflow for the EVD catheter. Additional sensors such as an intracranial pressure (ICP) sensor and/or a thermocouple can be inserted in the wall. To minimize the cross section, the ICP sensor and thermocouple can be nested alongside a respective conduit and the EVD catheter.

In accordance with a further object of the invention, the side port can have an angle between twelve and sixteen degrees away from the axis of the EVD catheter. An angle between twelve and sixteen degrees allows the probe to be extended at an angle without kinking the probe. In addition, an angle of at least twelve degrees allows the probe to extended deeply enough into surrounding tissue that it reaches brain tissue that is not affected by the EVD catheter but not so long to unnecessarily contact intervening brain tissue. Typically, by extending the probe to a distance of ten to fifteen millimeters (10-15 mm) the tip of the probe will be a lateral distance of less than one centimeter (<1 cm).

As stated, the ventricular catheter can include a thermocouple disposed in the wall. The thermocouple is sealed within the wall and connects by attaching a lead to the proximate end of the EVD catheter. The thermocouple is used to measure brain temperature around the ventricular catheter. Because the temperature of surrounding tissue and cerebral fluid are essentially the same temperature (any difference is negligible), the thermocouple can be placed in the wall of the EVD catheter and does not need to be extended into surrounding brain tissue.

As stated, the ventricular catheter can include an intracranial pressure (ICP) sensor. The ICP sensor continuously monitors ICP. The ICP sensor is disposed in the wall. The ICP sensor is attached to a monitor at the proximal end of the EVD catheter.

A further object of the invention is to provide a connector that is more durable, more sanitary, and easier to connect.

To achieve these objects, a part of a ring connector can be attached to a proximate end of the ventricular catheter. This allows the ventricular catheter to be quickly joined to a mating ring connector part on a connector to be attached to the ventricular catheter. The ring connector allows others additional connectors to be attached to the EVD catheter. The ring connection when connected is sealed to prevent pathogens from entering the EVD catheter and infecting the brain. Ring connectors are strong enough to remain connected even if the patient moves or unintentionally touches the catheter. The improved durability and sanitation extend the amount of time that the EVD catheter can remain inserted in the patient's brain. Typically, newer EVD catheters contain an antibiotic in the wall of the catheter to reduce the risk for infection. However, infection risks remain at the proximal end and along the connectors, using current technologies.

To facilitate quick connection of the ventricular catheter to a connector, each half of the ring connector can have an alignment mark made on it. The alignment marks are drawn to align with each other when the various leads (i.e. conduits, probes, ICP sensor, and thermocouple) align with leads in the connector. The use of alignment marks promotes quick connection with a reliable connection between the sensor and the respective monitor.

In ventricular catheters having an EVD catheter and two conduits, the ventricular catheter can include a three-to-one connector connected to the proximal end of the EVD catheter. The three-to-one connector has three lumen rotating valves at its proximal end. A first of the three lumen rotating valves is connected to the EVD catheter. A second of the three lumen rotating valves is connected to the first conduit and a third of the three lumen rotating valves is connected to the further conduit. Alignment markers can be placed on the EVD catheter and the distal end of the three-to-one connector. The alignment markers indicate when the conduits and respective lumen rotating valves are aligned.

The ventricular catheter can include markings on the EVD catheter. The markings indicate an insertion depth of the EVD catheter. The markings are useful to the surgeon to guarantee that the EVD catheter is inserted to the proper depth within the ventricles, either lateral or third.

A further object of the invention is to quickly insert the probe (i.e. sensor or conduit) into the conduit and extend it to the correct depth in the brain tissue. To meet this objective, the sensor can include markings that align with the proximate end of the EVD catheter to indicate when the sensor has been inserted to the proper depth. Likewise, the catheter can include markings that align with the proximate end of the EVD catheter to indicate when the catheter has been inserted to the proper depth.

A further object of the invention is to provide a ventricular catheter that can be used with various types of catheters. The catheter can be, for example, a microdialysis catheter or an infusion catheter. The microdialysis catheter continuously samples extracellular fluid from the surrounding brain tissue. The infusion catheter can be used for therapeutic or diagnostic purposes.

A further object of the invention is to provide a device that can be seen by common radiological procedures such as NMR (also know as MRI), CT scans, and x-rays. Accordingly, the distal type of the EVD catheter is radiologically opaque. This allows the depth of insertion of the EVD catheter to be easy confirmed.

Other features that are considered as characteristic for the invention are set forth in the appended claims.

Although the invention is illustrated and described herein as embodied in a ventricular catheter, it is nevertheless not intended to be limited to the details shown, because various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 2 is a cross-sectional view of the ventricular catheter taken along Line II-II in FIG. 1.

FIG. 3 is a partial side view of a distal tip of the ventricular catheter without having probes inserted and extended.

DETAILED DESCRIPTION OF THE INVENTION

Figure 1:
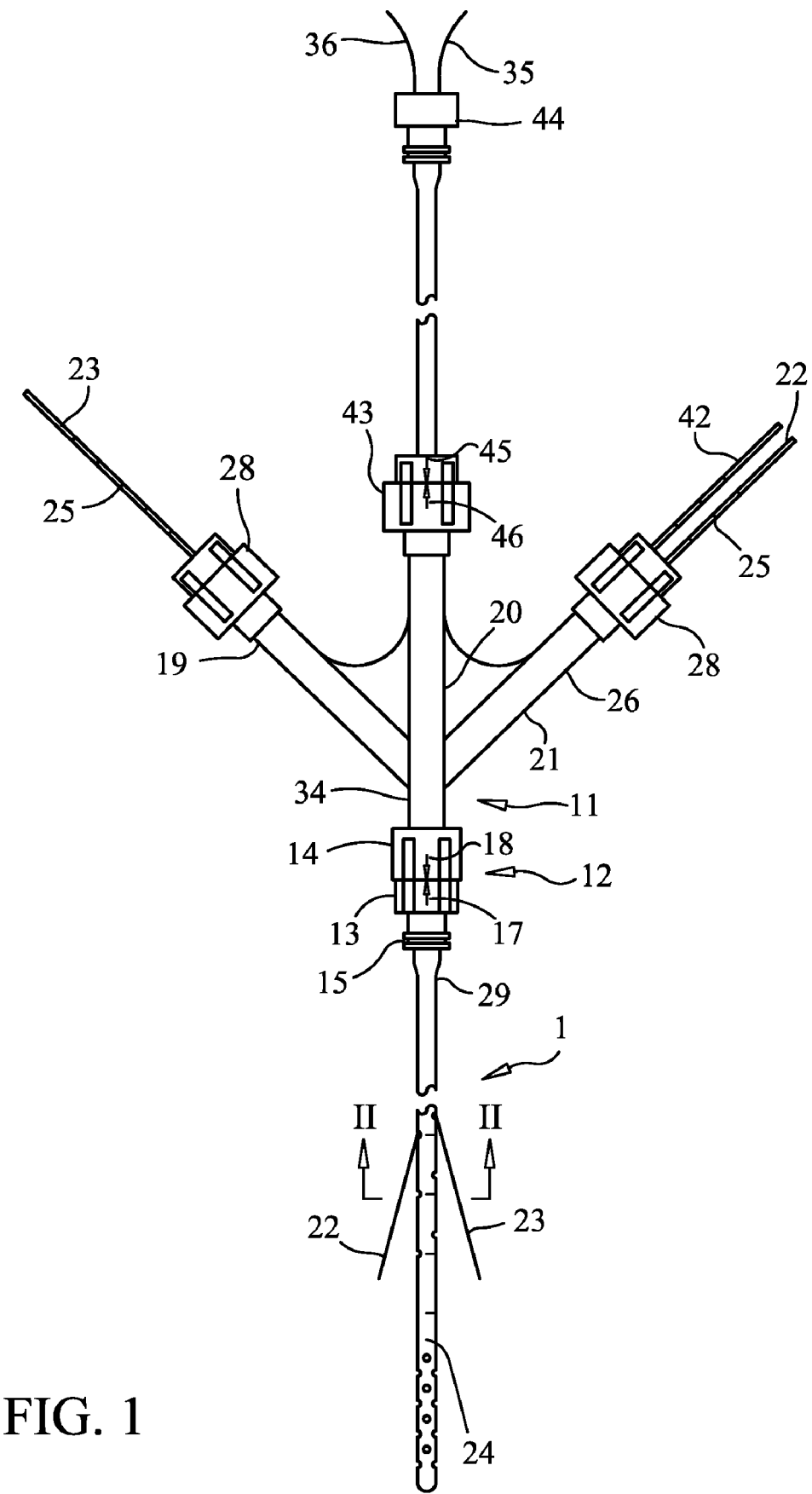
FIG. 1 is a side view of a ventricular catheter connected to a three-to-one connector.

Referring now to the figures of the drawing in detail and first, particularly, to FIG. 1 thereof, there is seen a ventricular catheter 1 according to the invention. The ventricular catheter 1 includes an external ventricular drainage (EVD) catheter 2; see FIGS. 2-4. The EVD catheter 2 is a generally elongated tube formed by a wall 3. The EVD catheter 2 preferably has a length of twenty centimeters (20 cm). This length allow for the distal tip 4 to be inserted into the brain and the proximate end 29 to be tunneled subcutaneously along the skull. The outer diameter of the EVD catheter 2 is preferably between 3.2 and 3.8 mm. The inner diameter of the EVD catheter 2 is preferably between 1.8 and 2.0 mm. The distal tip 4 of the EVD catheter 2 is made of a radio-opaque material.

FIG. 2 shows a cross section of the ventricular catheter 1 taken along Line II-II in FIG. 1. The overall crossection of the ventricular catheter 1 is oval shaped. The wall 3 of the ventricular catheter 1 defines the various conduits. The EVD catheter 2 is centrally disposed and consumes a majority of the cross sectional area of the ventricular catheter 1. On one side of the EVD catheter 2, along the long axis of the ventricular catheter 1, the first conduit 5 is formed. On the opposing side of the EVD catheter 2, along the long axis of the ventricular catheter 1, the second conduit 6 is formed by the wall 3. The diameter of the conduits 5 and 6 is preferably 1.2 mm.

FIG. 2 also shows a thermocouple 7 and ICP sensor 8 disposed in the wall 3. The thermocouple 7 and ICP sensor 8 are tucked alongside a respective one of the conduits 5 and 6 and the EVD catheter 2. The thermocouple 7 and ICP sensor 8 are embedded within the wall 3.

Figure 4:
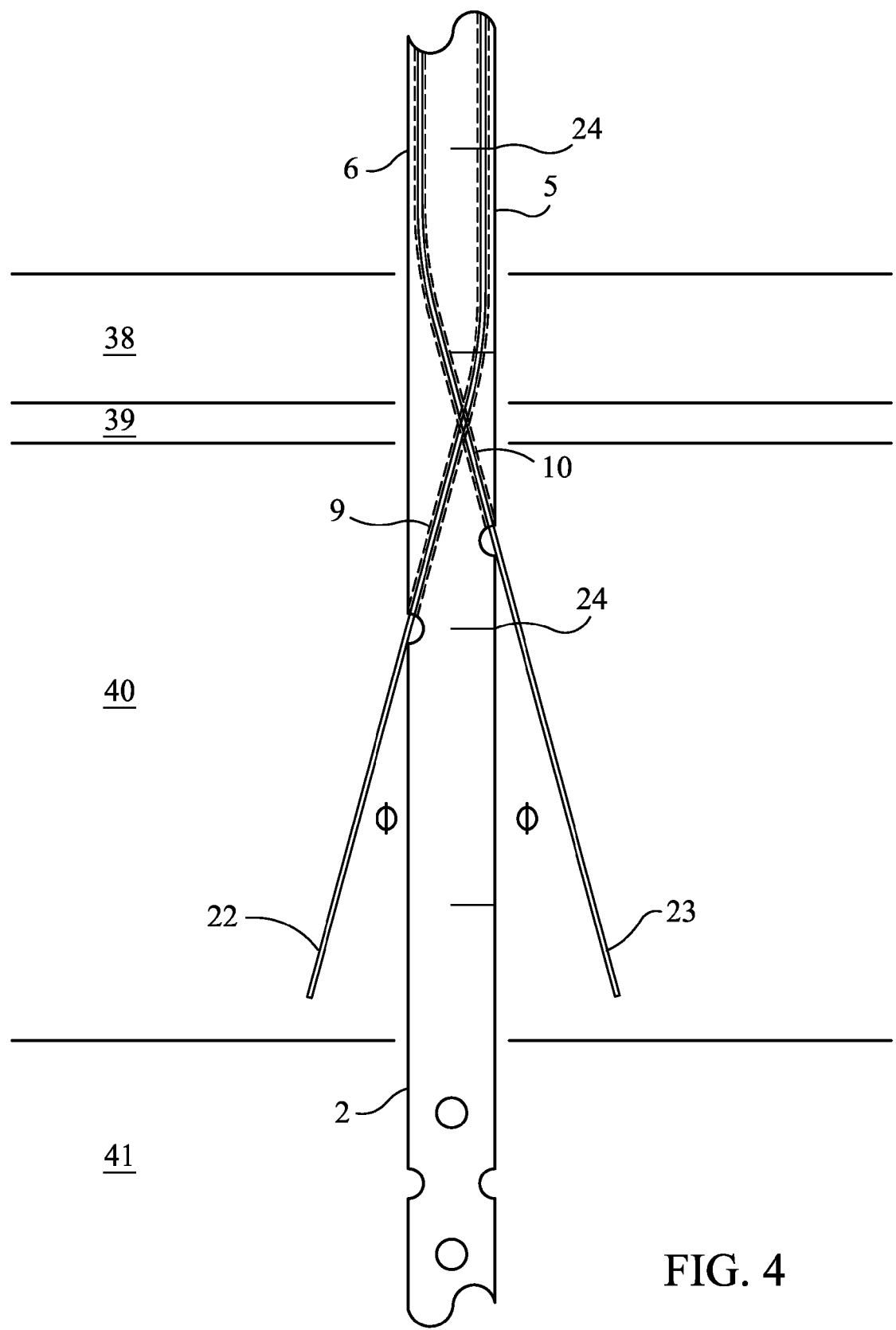
FIG. 4 is a partial side view as shown in FIG. 3 but with probes inserted into and extending from the conduits, which are shown in phantom.

FIGS. 3-4 show close-ups of the distal tip 4 of the EVD catheter 2. FIG. 3 shows the distal tip 4 of the EVD catheter without the probes 22 and 23 deployed. FIG. 4 shows the distal tip 4 of the EVD catheter with the probes 22 and 23 extended. The conduits 5 and 6, which are shown in phantom in FIG. 4, have angled side ports 9 and 10, respectively. The angled side ports 9 and 10 angle the probes and provide an egress for the probes 22 and 23 from the ventricular catheter 1. When the probes 22 and 23 are inserted in the conduits, the angle Φ of the side ports 9 and 10 cause the probes 22 and 23 to extend at the angle Φ as well.

FIG. 4 shows the distal end of the EVD catheter 2 with probes 22 and 23 inserted in the conduits 5 and 6 and extending from the side ports 9 and 10. The first conduit 5 has a side port 9. The side port 9 is at a twelve to sixteen degree (12-16°) angle Φ to the axis of the conduit 5. The side port 9 wraps halfway around the EVD catheter 2 before forming an opening in the wall 3. Likewise, a further side port 10 extends at a twelve to sixteen (12-16°) angle Φ to the axis of the conduit 6. The side port 10 wraps halfway around the EVD catheter 2 before forming an opening in the wall 12. The side ports 9 and 10 deflect and aim the probes 22 and 23 (i.e. catheter or probe) at the proper angle Φ into surrounding brain tissue 40.

The side ports 9 and 10 are disposed at a depth of four to four and one half centimeters (4-4.5 cm) from the distal tip 4 of the of EVD catheter 2. At this depth, the probes 22 and 23 (i.e. catheters and/or sensors) extending from the side ports 9 and 10 are aimed at the gray-white matter junction when the EVD catheter 2 is inserted into the ventricle 41.

FIG. 1 shows a ventricular catheter 1 with a three-to-one connector 11 connected to the proximal end 29 of the EVD catheter 2. The three-to-one connector 11 is used to branch one connection into three separate lines: Port I, Port II, and Port III. A ring connector 12 is used to connect the EVD catheter 2 to the three-to-one connector 11. The ring connector 12 has two parts 13 and 14. The first part 13 and the second part 14 mate with each other to form the ring connector 12. The first part 13 has an alignment mark 17 and the second part 14 has an alignment mark 18. The alignment marks 17 and 18 align when the connector conduits 19, 20, and 21 of the three-to-one connector 11 align with the conduits 5 and 6, EVD catheter 2, the thermocouple 7, and ICP sensor 8. The three-to-one connector 11 branches into three proximal branch conduits 19, 20, and 21. Leads, which are not shown, for the thermocouple and ICP pressure sensor run within the branch conduit 20.

"Port I" is the term for the central proximal branch conduit 20 and the associated ring connector 43. A catheter 37 for draining cerebrospinal fluid is connected to the ring connector 43. A thermocouple lead 35 runs in the wall of the conduit 37. Likewise, an ICP sensor lead 36 runs in the wall of the conduit 37. Alignment markers 45 and 46 are placed on each half of the ring connector 43 to help connect the leads 35 and 36 to the leads in the branch conduit 20. The catheter 37 has a ring connector 44 for connecting to a cerebrospinal collection bag, which is not shown. The leads 35 and 36 are connected to monitors, which are not shown, for displaying the intracranial pressure and temperature of the brain tissue.

"Port II" is the term given to the proximal branch conduits 19 that is connected to the conduit 5. "Port III" is the term given to the proximal branch conduit 21 that is connected to the conduit 6. Lumen rotating valves 28 are used to cap the branch conduits 19 and 20. The lumen rotating valves 28 allow for insertion and manipulation of the probes 22 and 23 but prevent cerebrospinal fluid from escaping.

When a probe 22 or 23 is inserted to a branch conduit 26 of the three-to-one connector 11, the probe 22 or 23 can be inserted into the respective conduit 5 or 6 and extended from the respective side port 9 or 10 in the brain tissue. The probe 22 or 23 can be connected at a distal end to an appropriate device or monitor, which is not shown.

While any combination of sensors and catheters may be used, the preferred embodiment shown uses an oxygen sensor and a microdialysis catheter as the probes 22 and 23. The oxygen sensor 23 measures a partial pressure of oxygen ($pO_2$) in the brain tissue. The microdialysis catheter 22 samples fluid from the brain tissue surrounding the EVD catheter and can be used to continuously monitor the pH, for example, of the fluid. The proximal end of the microdialysis catheter 22 is divided into two catheters: an inlet catheter 22 and an outlet catheter 42.

To insert the ventricular catheter 1, the desired location on the skull 38 of the patient is marked. The skin to be cut is locally anesthetized. An incision is made at the mark. A tripod drill is preferably used to drill orthogonally into the patient's skull 38. The tripod drill is helpful to guarantee that the angle of the drilling is proper. Next, the ventricular catheter 1 is inserted through the dura 39 into the brain tissue 40. Markers 24 on the EVD catheter 2 can be used to measure how far the EVD catheter 2 has been inserted. The distal tip 4 of the EVD catheter is also radiologically opaque and can be used to mark the depth of insertion of the EVD catheter 2 in the brain. Once the distal tip 4 of the EVD catheter 2 is inserted, a second incision is made. The proximal end 29 of the EVD catheter 2 is threaded from the first incision under the skin to the second incision where the proximal end 29 emerges. The first incision is then sutured. The distal end 34 of the three-to-one connector 11 is attached to the ventricular catheter 1. Leads are connected to the thermocouple 7 and the ICP sensor 8 and threaded from a respective lumen rotating valve 28. As needed, probes 22 and 23 can be inserted through one of the lumen rotating valves, through the three-to-one connector 11, into a respective conduit 5 or 6, to a respective side port 9 or 10, and into the brain tissue. Markers 25 on the probes 7 or 8 can be aligned with the proximal end 31 of the three-to-one connector 11, proximal end 29 of the EVD catheter 2, or proximal end 31 of the two-to-one connector 27 and used to measure the depth of insertion into the brain tissue. The probes 7 and/or 8 can be inserted as needed i.e. at a different time than the insertion of the EVD catheter 2.

During an insertion, the distal tip 4 is inserted into the ventricle (either lateral or third) to sample the intracranial pressure and relieve excess pressure. A typical insertion depth is six centimeters (6 cm) from the surface of the skull 38. At this depth the tip is about one centimeter (1 cm) in the ventricle 41. The probes 22 and 23 are to be inserted in the brain tissue 40. To do so, the side ports 9 and 10 optimally emerge one to one and five tenths centimeters (1.0 to 1.5 cm) below the dura 39. This provides room for the probes 22 and 23 to be extended but still remain in the brain tissue 40. Typically, the probes 22 and 23 are extended by a length of one to one and five tenths centimeters (1.0 to 1.5 cm).

I claim:

1. A ventricular catheter for extended multimodality monitoring of critical neurosurgical and neurological patients after traumatic brain injury (TBI), subarachnoid hemorrhages (SAH), and stroke, comprising:
    an external ventricular drainage (EVD) catheter formed by an enclosed wall;
    said wall having a conduit formed therein, said conduit opening at a side port of said wall at an angle to said EVD catheter, said angle being at least twelve degrees and not more than sixteen degrees and said angle being measured axially from a distal tip of said EVD catheter,
    said side port being formed in said wall at a depth that said port will be surrounded by brain tissue when the ventricular catheter is inserted; and
    said side port directing a probe to be extended from said conduit at said angle into the surrounding brain tissue to sample the brain tissue.

2. The ventricular catheter according to claim 1, wherein said probe is a sensor disposed in said conduit for sampling a brain tissue parameter and protruding from said side port at said angle.

3. The ventricular catheter according to claim 1, further comprising a catheter disposed in said conduit and extending from said port beyond said wall for interacting with surrounding brain tissue that would be uninjured by inserting said external ventricular drainage catheter.

4. The ventricular catheter according to claim 1, wherein said wall has a further conduit formed therein, said further conduit opening at a further side port of said wall at a further angle to said EVD catheter, said further side port being formed in said wall to allow a further probe to be extended from said further conduit at said further angle.

5. The ventricular catheter according to claim 1, wherein said wall has an oval cross section.

6. The ventricular catheter according to claim 1, further comprising a thermocouple for measuring brain temperature disposed in said wall.

7. The ventricular catheter according to claim 1, further comprising an intracranial pressure (ICP) sensor for continuous monitoring of ICP disposed in said wall.

8. The ventricular catheter according to claim 1, wherein:
    said EVD catheter has a proximal end; and
    a part of a ring connector is connected to said proximate end.

9. The ventricular catheter according to claim 7, wherein said part of said ring connector has an alignment marking for aligning said EVD catheter to a connector.

10. The ventricular catheter according to claim 4, wherein:
    said EVD catheter has a proximal end; and a first part of a ring connector is connected to said proximal end; and a three-to-one connector having a proximal end and a distal end and a second part of said ring connector at said distal end connected to said first part of said ring connector on said EVD catheter, said three-to-one connector dividing into three proximal branch conduits, a first of said proximal branch conduits being connected to said EVD catheter and being adapted for draining cerebrospinal fluid, a second of said proximal branch conduits being connected to a lumen rotating valve at said proximal end and said conduit in order to allow a probe to be inserted into said conduit via said ring connector and said second proximal branch conduit, and a third of said three lumen rotating valves being connected to a lumen rotating valve at said proximal end and said further conduit at a distal end in order to allow a probe to be inserted into said further conduit via said ring connector and said third proximal branch conduit.

11. The ventricular catheter according to claim 9, wherein:
said first part of said ring connector has a first alignment marking; and
said second part of said ring connector has a second alignment marking;
said first alignment marking and said second alignment marking being aligned to indicate when said second ring connector connects to said conduit and when said third ring connector connects to said further conduit.

12. The ventricular catheter according to claim 2, wherein said sensor is an oxygen sensor for sensing $pO_2$ in brain tissue surrounding said conduit.

13. The ventricular catheter according to claim 2, wherein said sensor is a carbon-dioxide sensor for measuring $pCO_2$ in brain tissue surrounding said conduit.

14. The ventricular catheter according to claim 3, wherein said sensor is a pH sensor for measuring pH in brain tissue surrounding said conduit.

15. The ventricular catheter according to claim 1, further comprising a marker on said EVD catheter marking an insertion depth of said EVD catheter.

16. The ventricular catheter according to claim 2, further comprising a marker on said sensor marking an insertion depth in said EVD catheter.

17. The ventricular catheter according to claim 3, further comprising a marker on said catheter marking an insertion depth in said EVD catheter.

18. The ventricular catheter according to claim 3, wherein said catheter is a microdialysis catheter for sampling extracellular fluid from the surrounding brain tissue.

19. The ventricular catheter according to claim 3, wherein said catheter is an infusion catheter for treatment or diagnosis.

20. The ventricular catheter according to claim 1, wherein said EVD catheter has a distal end, and said distal end is radiologically opaque.

21. The ventricular catheter according to claim 1, further comprising a probe disposed in said conduit and protruding from said port at said angle.

22. A ventricular catheter for extended multimodality monitoring of critical neurosurgical and neurological patients after traumatic brain injury (TBI), subarachnoid hemorrhages (SAH), and stroke, comprising:
an external ventricular drainage (EVD) catheter formed by an enclosed wall;
said wall having a conduit formed therein, said conduit opening at a side port of said wall at an angle to said EVD catheter,
said side port being formed in said wall at a depth that said port will be surrounded by brain tissue when the ventricular catheter is inserted;
a probe being disposed in said conduit and protruding from said port at said angle;
said side port directing said probe from said conduit at said angle into the surrounding brain tissue to sample the brain tissue, and
said probe being extended at least one centimeter from said port.

23. The ventricular catheter according to claim 21, wherein said probe is extended no further than one-and-one-half centimeters from said port.

24. A ventricular catheter for extended multimodality monitoring of critical neurosurgical and neurological patients after traumatic brain injury (TBI), subarachnoid hemorrhages (SAH), and stroke, comprising:
an external ventricular drainage (EVD) catheter formed by an enclosed wall;
said wall having a conduit formed therein, said conduit opening at a side port of said wall at an angle to said EVD catheter,
said side port being formed in said wall at a depth that said port will be surrounded by brain tissue when the ventricular catheter is inserted;
a probe being disposed in said conduit and protruding from said port at said angle;
said side port directing said probe from said conduit at said angle into the surrounding brain tissue to sample the brain tissue, and
said probe being extended no further than one-and-one-half centimeters form said port.

25. A ventricular catheter for extended multimodality monitoring of critical neurosurgical and neurological patients after traumatic brain injury (TBI), subarachnoid hemorrhages (SAH), and stroke, comprising:
an external ventricular drainage (EVD) catheter formed by an enclosed wall;
said wall having a conduit formed therein, said conduit opening at a side port of said wall at an angle to said EVD catheter,
said side port being formed in said wall at a depth that said port will be surrounded by brain tissue when the ventricular catheter is inserted;
a probe being disposed in said conduit and protruding from said port at said angle;
said side port directing said probe from said conduit at said angle into the surrounding brain tissue to sample the brain tissue, and
a tip of said probe being at a distance no greater than one centimeter from said wall.

26. A ventricular catheter for extended multimodality monitoring of critical neurosurgical and neurological patients after traumatic brain injury (TBI), subarachnoid hemorrhages (SAH), and stroke, comprising:
an external ventricular drainage (EVD) catheter formed by an enclosed wall;
said wall having a conduit formed therein, said conduit opening at a side port of said wall at an angle to said EVD catheter,
said side port being formed in said wall at a depth that said port will be surrounded by brain tissue when the ventricular catheter is inserted;
a probe being disposed in said conduit and protruding from said port at said angle;

said side port directing said probe from said conduit at said angle into the surrounding brain tissue to sample the brain tissue, and a tip of said probe being at a distance of at least two microns from said wall.

27. The ventricular catheter according to claim 24, wherein said tip of said probe is at a distance of at least four-hundred microns from said wall.

28. The ventricular catheter according to claim 24, wherein said catheter extends no more than one centimeter from said wall.

29. The ventricular catheter according to claim 20, wherein a tip of said probe is at a distance from said wall to reach brain tissue that is not damaged during insertion of said EVD catheter into the brain tissue.

30. The ventricular catheter according to claim 20, wherein probe extends from said port to a length where said probe reaches brain tissue that is not damaged during insertion of said EVD catheter into the brain tissue.

31. A ventricular catheter for extended multimodality monitoring of critical neurosurgical and neurological patients after traumatic brain injury (TBI), subarachnoid hemorrhages (SAH), and stroke, comprising:

an external ventricular drainage (EVD) catheter formed by an enclosed wall, said wall having an oval cross section, said oval cross section having an eccentric axis; and said wall having a conduit formed therein, said conduit opening at a side port of said wall at an angle to said EVD catheter, said conduit transversing said eccentric axis, said side port being formed in said wall at a depth that said port will be surrounded by brain tissue when the ventricular catheter is inserted; and said side port being configured to direct a probe to be extended from said conduit at said angle into the surrounding brain tissue to sample the brain tissue.

32. A ventricular catheter for extended multimodality monitoring of critical neurosurgical and neurological patients after traumatic brain injury (TBI), subarachnoid hemorrhages (SAH), and stroke, comprising:

an external ventricular drainage (EVD) catheter formed by an enclosed wall;

said wall having a conduit formed therein, said conduit opening at a side port of said wall at an angle to said EVD catheter, said side port being formed in said wall at a depth that said port will be surrounded by brain tissue when the ventricular catheter is inserted;

said side port directing a probe to be extended from said conduit at said angle into the surrounding brain tissue to sample the brain tissue, said wall having an elliptical cross section with an eccentric axis;

said conduit and said further conduit transversing said eccentric axis; and said conduit and said further conduit being disposed on laterally opposing sides of said EVD catheter.

33. A ventricular catheter for extended multimodality monitoring of critical neurosurgical and neurological patients after traumatic brain injury (TBI), subarachnoid hemorrhages (SAH), and stroke, comprising:

an external ventricular drainage (EVD) catheter formed by an enclosed wall;

said wall having a conduit formed therein, said conduit opening at a side port of said wall at an angle to said EVD catheter, said side port being formed in said wall at a depth that said port will be surrounded by brain tissue when the ventricular catheter is inserted;

said side port directing a probe to be extended from said conduit at said angle into the surrounding brain tissue to sample the brain tissue; and said port being formed no more than four and one half centimeters from a distal end of said EVD catheter.

* * * * *